(12) United States Patent
Kim et al.

(10) Patent No.: US 8,920,754 B2
(45) Date of Patent: Dec. 30, 2014

(54) CUVETTE

(75) Inventors: Joon-Won Kim, Pohang (KR);
Wan-Kyun Chung, Pohang (KR)

(73) Assignee: Postech Academy-Industry Foundation, Pohang-City (KR)

( * ) Notice: Subject to any disclaimer, the term of this patent is extended or adjusted under 35 U.S.C. 154(b) by 0 days.

(21) Appl. No.: 13/498,521

(22) PCT Filed: Oct. 14, 2010

(86) PCT No.: PCT/KR2010/007063
§ 371 (c)(1),
(2), (4) Date: Mar. 27, 2012

(87) PCT Pub. No.: WO2011/046379
PCT Pub. Date: Apr. 21, 2011

(65) Prior Publication Data
US 2012/0189510 A1 Jul. 26, 2012

(30) Foreign Application Priority Data

Oct. 15, 2009 (KR) .................. 10-2009-0098335
Oct. 14, 2010 (KR) .................. 10-2010-0100535

(51) Int. Cl.
| | | |
|---|---|---|
| *G01N 21/05* | (2006.01) | |
| *G01N 21/03* | (2006.01) | |
| *B01L 3/00* | (2006.01) | |
| *G01N 21/11* | (2006.01) | |
| *B01L 99/00* | (2010.01) | |
| *G01N 1/10* | (2006.01) | |

(52) U.S. Cl.
CPC ............ *G01N 21/03* (2013.01); *B01L 3/50857* (2013.01); *G01N 21/11* (2013.01); *B01L 99/00* (2013.01); *B01L 3/5082* (2013.01); *B01L 2400/0688* (2013.01); *G01N 2021/115* (2013.01)

USPC .......................................... 422/554; 356/246

(58) Field of Classification Search
USPC .......................................................... 422/554
See application file for complete search history.

(56) References Cited

U.S. PATENT DOCUMENTS

| | | | | |
|---|---|---|---|---|
| 5,731,212 | A * | 3/1998 | Gavin et al. .................... | 436/526 |
| 6,249,345 | B1 * | 6/2001 | Kraack et al. ................. | 356/246 |
| 7,224,448 | B2 * | 5/2007 | Ji ................................... | 356/244 |
| 2007/0081155 | A1 * | 4/2007 | Schembri et al. ............. | 356/246 |

FOREIGN PATENT DOCUMENTS

| | | |
|---|---|---|
| JP | 03-223674 | 10/1991 |
| JP | 2000-500567 | 1/2000 |

(Continued)

*Primary Examiner* — Jill Warden
*Assistant Examiner* — Brittany Fisher
(74) *Attorney, Agent, or Firm* — Lexyoume IP Meister, PLLC

(57) ABSTRACT

An exemplary embodiment of the present invention relates to a cuvette of which an inner space thereof is easily cleansed while minimizing its inner space.

A cuvette according to an exemplary embodiment of the present invention includes an upper portion having an inlet and forming a first inner space; a middle portion following the first inner space and forming a second inner space that is smaller than the first inner space; and a lower portion following the second inner space and forming a through hole having an interior diameter that is narrower than a cross-section of the second inner space.

Accordingly, the through hole functions as a valve to stop the solution when the solution is divided to the inner space for the test, and after the test, the inlet is pressed such that the through hole functions as a nozzle when cleansing such that the solution may be exhausted therefrom.

17 Claims, 12 Drawing Sheets

(56) References Cited

FOREIGN PATENT DOCUMENTS

| JP | 2002-243632 | 8/2002 |
| JP | 2005-195540 | 7/2005 |
| JP | 2007-285847 | 11/2007 |
| WO | 2009/046924 | 4/2009 |
| WO | 2009/121556 | 10/2009 |

* cited by examiner

CUVETTE

TECHNICAL FIELD

The present invention relates to a cuvette. More particularly, the present invention relates to a cuvette used as a container for a spectroscope test for a biochemical test.

BACKGROUND ART

In general, a biochemical test simultaneously performs a test on a plurality of specimens such that it is necessary to reduce the amount of a reagent used. Accordingly, efforts have been made to reduce the size of the container used in the biochemical test, that is, the inner space thereof.

Figure 1:
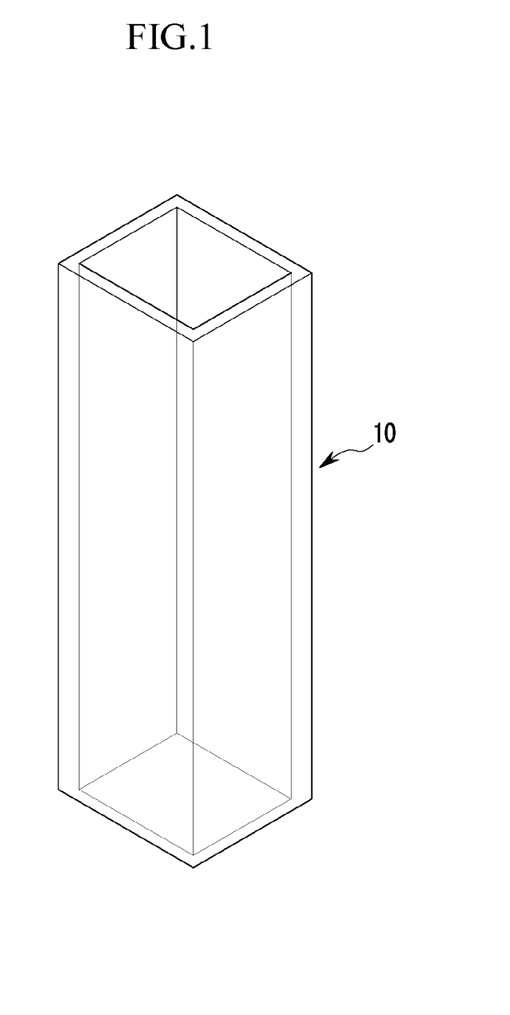
FIG. 1 and FIG. 2 are photos of a container for a biochemical test according to a conventional art.
Figure 2:
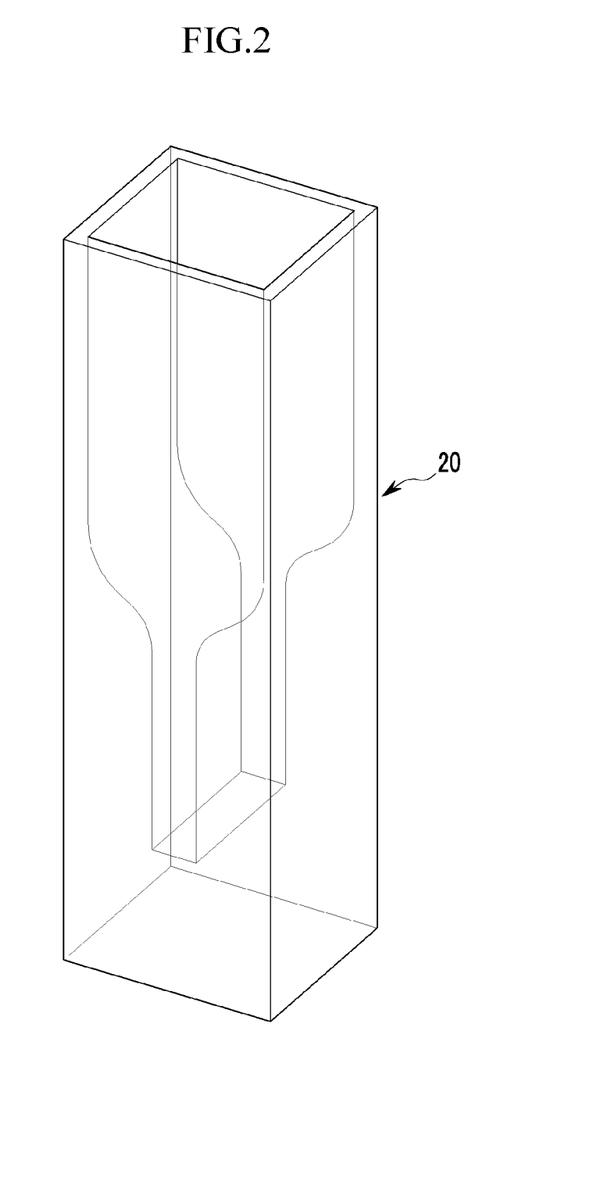

Referring to FIG. 1 and FIG. 2, the container for a biochemical test has been changed into a streamlined inverted triangle (FIG. 2) shaped container 20 from a cuboid shaped (FIG. 1) container 10. However, as the inner space of the container is reduced, work to clean the inner space of the container for reuse becomes difficult. The streamlined inverted triangle shape reduces the inner space compared to the cuboid shape such that the usage amount of the reagent is reduced, but cleaning of the inner space of the container becomes more difficult.

A cuvette used for a biochemical test is made of a structure having an inlet for division of the reagent and the specimen, that is, a mixture solution, at one side, and closing and sealing a region besides the inlet. For reuse of the cuvette, a process of cleaning the inner space of the cuvette repeats dividing a cleansing solution to the inner space through the inlet and drawing in the divided cleaning solution. That is, the cleansing process uses a dispensing nozzle dividing the cleansing solution and a suction nozzle drawing in the cleansing solution.

However, as the inner space of the container is small, when repeating the processes of dividing the cleansing solution to the inner space and drawing in the cleansing solution from the inner space, a possibility of a foreign material remaining at the inner space and the bottom of the cuvette is increased, or complete cleansing is difficult.

Accordingly, compared with the cuboid shaped (FIG. 1) container 10, the cuvette of the streamlined inverted triangle (FIG. 2) shaped container 20 that reduces the inner space may reduce the amount of reagent used for the biochemical test, however cleansing for reuse is difficult, and is thereby mainly used in a disposable form.

The above information disclosed in this Background section is only for enhancement of understanding of the background of the invention and therefore it may contain information that does not form the prior art that is already known in this country to a person of ordinary skill in the art.

DISCLOSURE

Technical Problem

An exemplary embodiment of the present invention provides a cuvette of which an inner space thereof is easily cleaned while minimizing the inner space.

A cuvette made of a container including a sample solution and used for a spectroscope test according to an exemplary embodiment of the present invention includes: an upper portion having an inlet and forming a first inner space of the container; and a lower portion formed to communicate with the first inner space and forming a through hole having a horizontal cross-section of an area that is narrower than the horizontal cross-section of the first inner space.

The through hole may function as a valve that is closed by a capillary force and is opened by an added pressure.

The through hole may be formed such that surface tension acting between the sample solution and an inner surface of the through hole is equal or larger than gravity applied to the sample solution included in the container.

The through hole and the inlet may satisfy the condition below, $$\rho g H \le -2\sigma\left(\frac{\cos\theta_i}{w_2} + \frac{\cos\theta_i}{h_2} - \frac{\cos\theta_r}{w_1} - \frac{\cos\theta_r}{h_1}\right),$$

wherein $w_1$ is a width of an inlet of an upper portion, $h_1$ is a thickness of an inlet of an upper portion, $w_2$ is a width of a through hole, $h_2$ is a thickness of a through hole, $\rho$ is density of a liquid, g is gravity acceleration, and H is a difference of a height in a gravity direction formed by a liquid.

The cuvette may further include a middle portion connected to the first inner space and forming a smaller second inner space than the first inner space, and the through hole of the lower portion may be connected to the second inner space and have a narrower horizontal cross-section than the horizontal cross-section of the second inner space.

The second inner space formed in the middle portion may have a thickness L set up in a path direction of measured light of more than a minimum depth that the light is transmitted, and may be formed by satisfying a width W set up to be at least larger than the size of a spot of the light. The width of the second inner space may be larger than the width of the sensor.

For the through hole, the horizontal cross-section of the lower portion may be formed with a quadrangle shape or a circular shape. Multiple through holes may be formed. For the through hole, the horizontal cross-section of the lower portion may be formed with a slit shape. The through hole may have an inner surface that is curved or is formed with a minute structure.

The through hole may further include a non-wetting coating layer formed at the inner surface thereof. The cuvette may be formed by combining a body unit of which the upper portion and the middle portion are integrally formed, and a through hole unit forming the lower portion. The through hole unit may be formed of a non-wetting material.

The lower portion may further include a groove connected to the through hole. The groove may be formed and connected in a direction vertical to the through hole. The groove may be formed singularly or in plural with respect to an entire length of the through hole.

Advantageous Effects

As described above, according to an exemplary embodiment of the present invention, the first inner space is formed at the upper portion, and the through hole is formed at the lower portion such that the inner space of the cuvette is minimized, and thereby the usage amount of the reagent is reduced and the cost may be reduced.

Also, the through hole functions as a valve to stop the solution when the solution is divided to the inner space for the test, and after the test, the inlet is pressed such that the through hole functions as a nozzle when cleansing such that the solution may be exhausted. Accordingly, the division and the pressure exhausting of the cleansing solution are repeated such that the inner space may be easily cleansed.

DESCRIPTION OF REFERENCE NUMERALS INDICATING PRIMARY ELEMENTS IN THE DRAWINGS

| | |
|---|---|
| 100: cuvette | 11: first inner space |
| 12: upper portion | 13: inlet |
| 21: second inner space | |
| 22: middle portion | 23, 33: bottom surface |
| 31, 311, 312, 313, 314: through hole | 32: lower portion |
| 101: body unit | 103: through hole unit |
| l: light | H: height |
| L: thickness | P: measuring position |
| W: width | θ: contact angle |
| β: expansion angle (expansion angle) | 34: groove |

MODE FOR INVENTION

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention. The drawings and description are to be regarded as illustrative in nature and not restrictive. Like reference numerals designate like elements throughout the specification.

Figure 3:
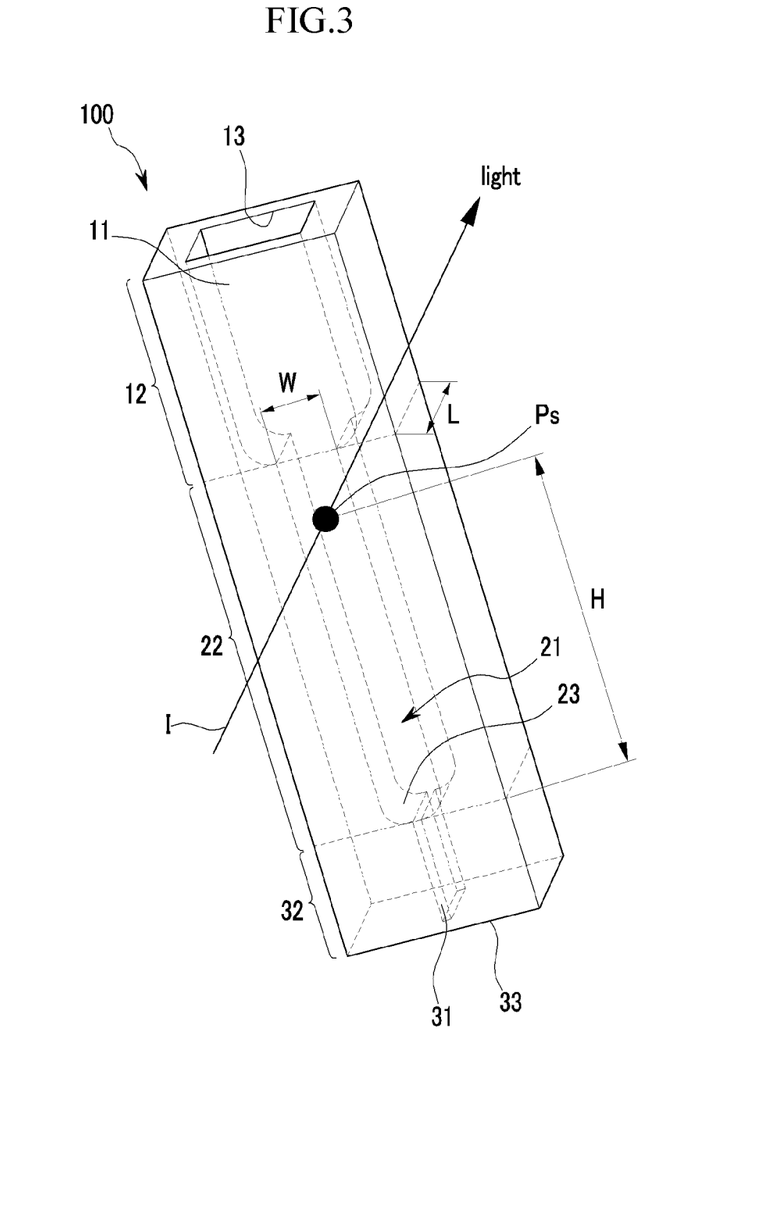
FIG. 3 is a perspective view of a cuvette according to an exemplary embodiment of the present invention.

FIG. 3 is a perspective view of a cuvette according to an exemplary embodiment of the present invention. A cuvette 100 according to the present exemplary embodiment includes an upper portion 12 forming a first inner space 11 that is set relatively largely at an upper portion thereof, a middle portion 22 forming a second inner space 21 connected to the first inner space 11 and set to be smaller than the first inner space 11, and a lower portion 32 forming a through hole 31 to the second inner space 21 and connected with a path that is narrower than the second inner space 21.

The upper portion 12 has an inlet 13 formed by extending the first inner space 11 for a specimen and a reagent, that is, a sample solution to be put into the first inner space 11 at an upper side thereof. The inlet 13 and the first inner space 11 have a larger width than the second inner space 21, thereby allowing easy inserting of the solution. Also, the inlet 13 is connected to hardware of test equipment that will be applied with the cuvette 100 of the present exemplary embodiment such that a divided solution flows into the first inner space 11.

The middle portion 22 is a portion determined according to performance of the test equipment. That is, the shape of the second inner space 21 is related to the performance of the test equipment. For example, in the middle portion 22, a thickness L of the second inner space 21 is set up as a path direction through which light l is passed, and the second inner space 21 has a thickness such that it is capable of measuring a change of a light absorption ratio of the solution by a mounted sensor, that is, a thickness of more than a Minimum depth such that it is capable of measuring the absorption ratio change of the light according to a concentration after the light l is passed through the test solution. In general, in a spectrophotometer as test equipment, to reduce an error by light reflected from the bottom surface 33, a spot Ps of the light l is positioned and measured at a position separated from a bottom surface 33 and a height H of the separated measuring position is set upwards by more than about 10 cm as an example, to prevent interference of the light l. The width W of the second inner space 21 is larger than the width of a sensor (not shown) included in the test equipment and is larger than the size of the spot S of the light l at a minimum. As described above, although the thickness L, the height H, and the width W has a condition, the cuvette 100 of the first exemplary embodiment may form the second inner space 21 of a very small volume compared with the conventional cuvette (referring to FIG. 1 and FIG. 2). As the volume of the second inner space 21 is decreased, the usage amount of the reagent for the test is reduced, thereby reducing cost.

The lower portion 32 has the through hole 31 connected to the second inner space 21 of the middle portion 22, in detail, to a bottom surface 23 of the second inner space 21, thereby functioning as a valve for preventing the solution from flowing down during the division of the solution and the biochemical test, and simultaneously, as a nozzle for easily exhausting the solution during cleansing after the discharging test. That is, the lower portion 32 and the through hole 31 performs a function of a capillary valve. In the functional aspect of the valve preventing flow of the solution, the through hole 31 may endure a further larger pressure, that is, a further larger weight of the solution as the size of the interior diameter is made smaller. However, in the aspect of exhausting the solution by applying pressure to the inlet 13 in the cleansing process, the through hole 31 is advantageous as the interior diameter is large. Accordingly, the interior diameter of the through hole 31 may be determined as the maximum size in the range for preventing various solutions from flowing down in a state that the pressure is not applied simultaneously while processing the cleansing by applying the pressure.

The lower portion 32 includes the through hole 31 such that the solution is not absorbed through the inlet 13 after the test, and the solution is exhausted into the through hole 31 by applying pressure to the injected solution through the inlet 13, thereby easily cleansing the first and second inner spaces 11 and 21. That is, the cuvette 100 of the present exemplary embodiment needs a dispensing nozzle to cleanse the inner space, that is, the first and second inner spaces 11 and 21 and the inner surface of the through hole 31, however a suction nozzle is not required. Accordingly, the cuvette 100 of the present exemplary embodiment reduces the inner space compared with the conventional art without the through hole at the bottom surface such that the reagent and the test cost are reduced and the cleansing work of the inner space for reuse is convenient.

Figure 4:
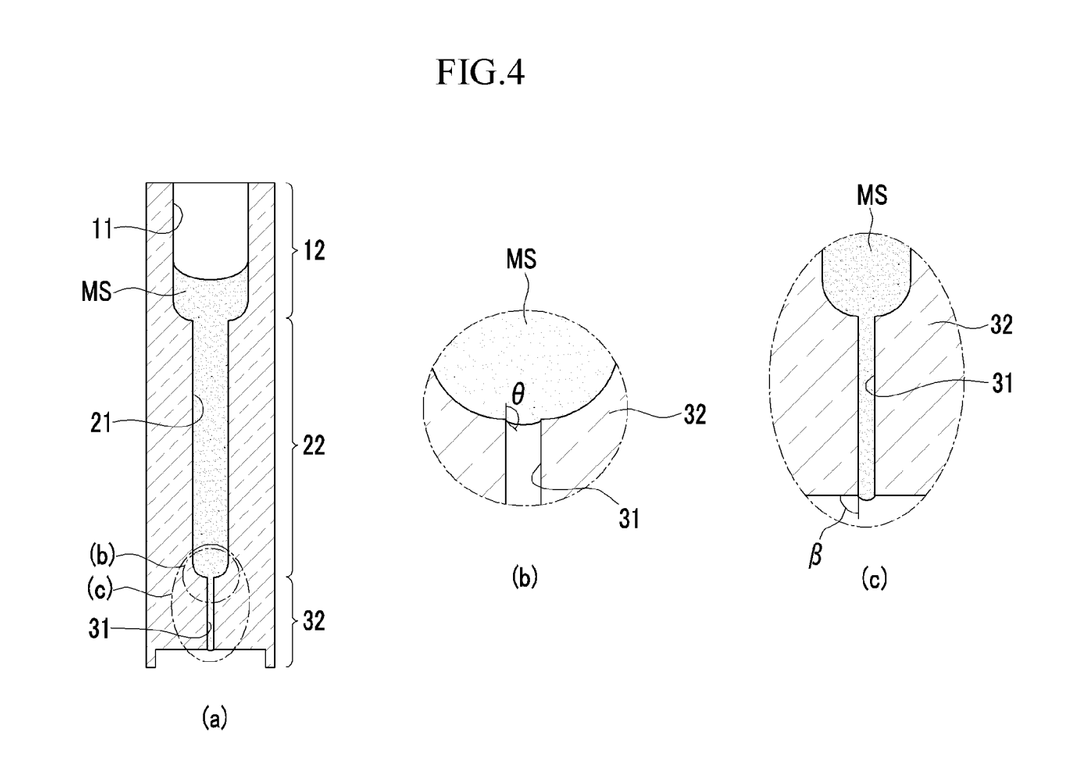
FIG. 4 and FIG. 8 are cross-sectional views showing an operation principle of a cuvette according to an exemplary embodiment of the present invention.
Figure 8:
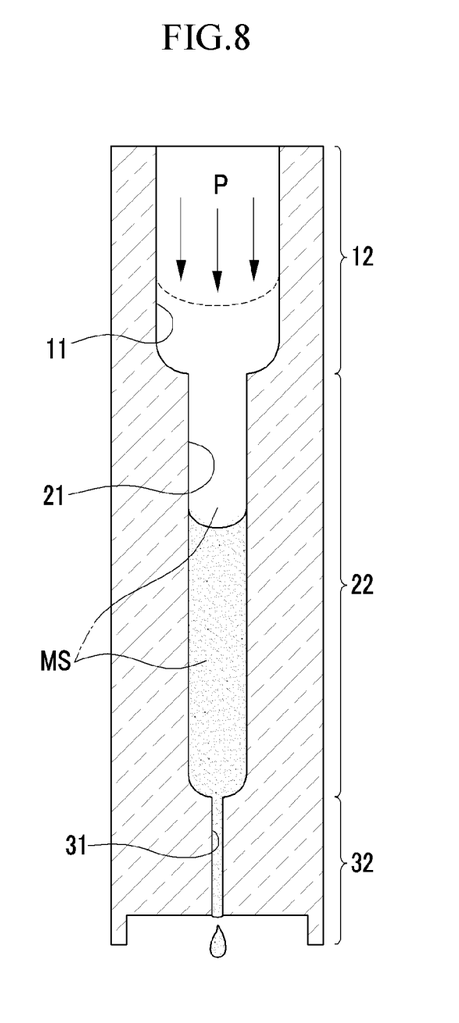

FIGS. 4(*a*) to (*c*) and FIG. 8 are cross-sectional views showing an operation principle of a cuvette according to an exemplary embodiment of the present invention.

Firstly, referring to FIGS. 4(*a*) to (*c*), in the process of the biochemical test, through the dispensing nozzle (not shown), a solution MS mixed with the specimen and the reagent is divided to the cuvette 100 of the present exemplary embodiment by a predetermined amount (FIG. 4(*a*)). At this time, the solution MS is filled to a portion of the second inner space 21 and the first inner space 11 and is not passed through the through hole 31, and the blocked state is maintained (FIG. 4(*b*)).

As a characteristic of the surface of the second inner space 21 contacting the solution MS, for example, according to a contact angle θ of the solution MS and a surface tension of the solution MS, the solution MS does not flow down through the through hole 31 but is stopped. For example, when the contact angle θ of the solution MS is larger than 90 degrees, the solution MS is stopped at the inlet of the through hole 31 (FIG. 4 (*b*)).

When the contact angle θ of the solution MS is smaller than 90 degrees, the solution MS is passed through the through hole 31 and is stopped at the end portion of the through hole 31, and when an expansion angle (β) of a wall surface meeting in the end portion of the through hole 31 is more than 90 degrees even though the solution MS is passed through the through hole 31, the solution MS does not flow down further unless subjected to a predetermined pressure (FIG. 4(*c*)).

That is, the cuvette 100 of the present exemplary embodiment firstly stops the solution MS at the end of the second inner space 21 connected to the through hole 31, also secondly stops the solution MS having flowed down from the second inner space 21 in the through hole 31, and thereby the biochemical test may be performed even though the lower portion 32 of the cuvette 100 includes the through hole 31. As described above, in a state that a small amount of the mixture solution MS of the specimen and the reagent is divided to the cuvette 100 and is stopped in the second inner space 21, the biochemical test is performed.

Meanwhile, to set up the size of the through hole 31 for the through hole 31 of the cuvette 100 according to the present exemplary embodiment to have the function of a valve, the length at which the solution contacts the wall surface of the cuvette 100 and a relation of the surface tension and the contact angle in the boundary (the upper portion and the lower portion) of the height H filled with the solution and the received solution may be set up.

Figure 5:
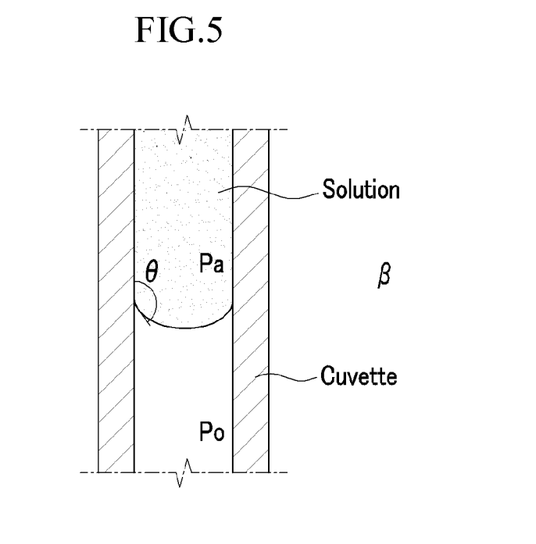
FIG. 5 to FIG. 7 are schematic views to explain a condition to form an inlet and a through hole of a cuvette according to an exemplary embodiment of the present invention when considering surface tension and gravity.

Referring to FIG. 5, in general, in a case of a circular tube, the Young-Laplace Equation represented by Equation 1 as follows is used.

$$P_a - P_o = -2\sigma \frac{\cos\theta}{r} \quad \text{[Equation 1]}$$

Po: outer pressure of a liquid (air)
Pa: inner pressure of a liquid
r: radius of a circular tube
σ: surface tension of a liquid
α: contact angle of a liquid in a tube inner wall Also, in a case of a square channel having a width w of a cross-section and a thickness h, the Young-Laplace Equation is represented by Equation 2 as follows.

$$P_a - P_o = -2\sigma\left(\frac{\cos\theta}{w} + \frac{\cos\theta}{h}\right) \quad \text{[Equation 2]}$$

By applying this equation to the through hole of the cuvette of an exemplary embodiment of the present invention, the size of the through hole of a holding condition for preventing the solution received inside the cuvette from flowing down may be obtained.

Figure 6:
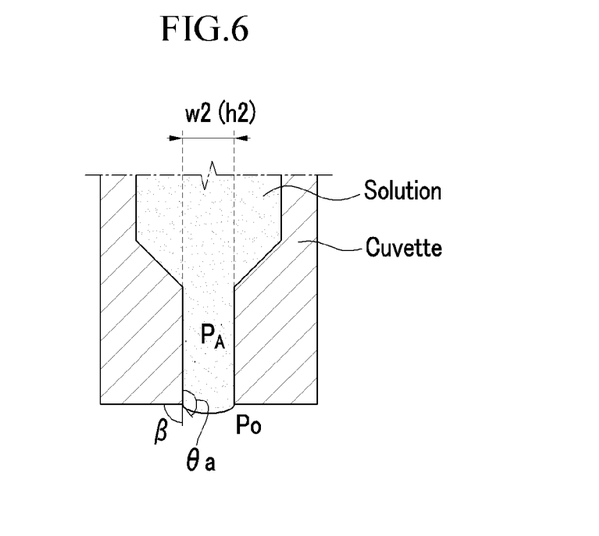

That is, when the solution is passed through the through hole of the lower portion and is formed at the end portion, the through hole may function as a capillary burst valve while the solution meet the increased cross-section. In this case, the inner pressure may be sustained until the surface of the solution meets the surrounding wall, and an effect that the contact angle of the solution is increased by the angle of the bottom surface of the end portion of the lower portion may be obtained. In this relation equation, the contact angle is determined as a value of which the angle of the bottom surface is added to an advancing contact angle of the solution, and when the combination of the two angles is more than 180 degrees, 180 degrees is applied. A relation equation obtained as described above with reference to FIG. 6 is represented by Equation 3.

$$P_A - P_O = -2\sigma\left(\frac{\cos\theta_i}{w_2} + \frac{\cos\theta_i}{h_2}\right) \quad \text{[Equation 3]}$$

$$\theta_i = \min\{\theta_a + \beta, 180°\}$$

β: angle between a bottom surface and a channel in an end portion of a through hole
$P_A$: inner pressure of a liquid (solution) in an end portion of a through hole of a cuvette
$w_2$: width of a through hole
$h_2$: thickness of a through hole
$θ_a$: advancing contact angle of a liquid (solution) in an end portion of a through hole of a cuvette.

Figure 7:
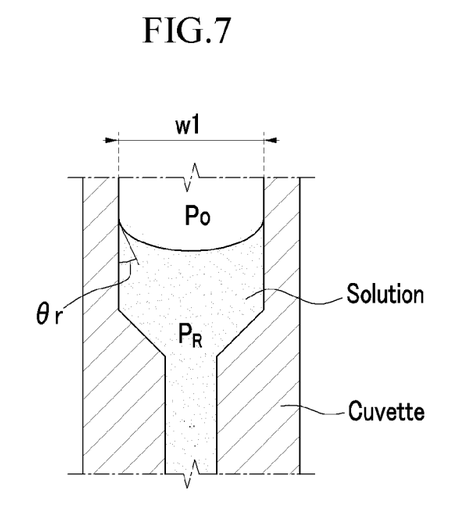

If a capillary force is generated to the solution when the solution contacts the upper portion while performing the valve function, the contact angle is applied with a receding contact angle of the solution. A relation equation obtained as described above with reference to FIG. 7 is represented by Equation 4.

$$P_R - P_O = -2\sigma\left(\frac{\cos\theta_r}{w_1} + \frac{\cos\theta_r}{h_1}\right) \quad \text{[Equation 4]}$$

$P_R$: inner pressure of a liquid (solution) in an upper portion of a cuvette
θr: receding contact angle of a liquid (solution) in an upper portion of a cuvette Accordingly, when receiving the solution to the cuvette, for holding the solution so as to not flow down by the through hole of the lower portion functioning as the valve, the surface tension acting between the sample solution and the inner surface of the through hole is constituted to be equal or larger than gravity acting on the sample solution filled in the cuvette. That is, the capillary force in the through hole must be equal to or larger than hydrostatic pressure due to the height of the solution in a gravity direction. Accordingly, Equation 5 may be obtained from a difference between Equation 3 and Equation 4 below.

$$P_A - P_R \leq -2\sigma\left(\frac{\cos\theta_i}{w_2} + \frac{\cos\theta_i}{h_2} - \frac{\cos\theta_r}{w_1} - \frac{\cos\theta_r}{h_1}\right) \quad \text{[Equation 5]}$$

$$P_A - P_R = \rho g H$$

$w_1$: width of an inlet of an upper portion
$h_1$: thickness of an inlet of an upper portion
$w_2$: width of a through hole
$h_2$: thickness of a through hole
$\rho$: density of a liquid
g: gravity acceleration
H: height difference of a gravity direction formed by a liquid Accordingly, when the width and the thickness of the through hole have a square cross-sectional ($w_2=h_2=S$), Equation 5 may be equal to Equation 6 below. Here, S is a length of one edge of the square hole and means a value that is the same as a diameter D of a circular hole.

$$\rho g H = P_A - P_R \leq -2\sigma\left(\frac{\cos\theta_i}{S} + \frac{\cos\theta_i}{S} - \frac{\cos\theta_r}{w_1} - \frac{\cos\theta_r}{h_1}\right) \quad \text{[Equation 6]}$$

$$\rho g H - 2\sigma\left(\frac{\cos\theta_r}{w_1} + \frac{\cos\theta_r}{h_1}\right) \leq \frac{-4\sigma\cos\theta_i}{S}$$

$$S \leq \frac{-4\sigma\cos\theta_i}{\rho g H - 2\sigma\left(\frac{\cos\theta_r}{w_1} + \frac{\cos\theta_r}{h_1}\right)}$$

Accordingly, in order for the through hole of the cuvette to perform the valve function, it is preferable that it is less than the length S of one edge of the through hole obtained from Equation 6.

That is, in order for the through hole of the cuvette according to the present exemplary embodiment to perform the valve function, the inlet and the through hole may be designed to be satisfied with a condition of Equation 7 below.

$$\rho g H \leq -2\sigma\left(\frac{\cos\theta_i}{w_2} + \frac{\cos\theta_i}{h_2} - \frac{\cos\theta_r}{w_1} - \frac{\cos\theta_r}{h_1}\right) \quad \text{[Equation 7]}$$

$w_1$: width of an inlet of an upper portion
$h_1$: thickness of an inlet of an upper portion
$w_2$: width of a through hole
$h_2$: thickness of a through hole
$\rho$: density of a liquid
g: gravity acceleration
H: difference of a height of a gravity direction formed by a liquid Referring to FIG. 8, after finishing the test, the cuvette 100 is cleansed. In the cleansing process, if a predetermined pressure P (for example, compressed air) is applied at the inlet 13 of the upper portion 12 of the cuvette 100, the solution MS that is stopped at the second inner space 21 is exhausted under the lower portion 32 through the through hole 31. Also, after the cleansing solution is inserted through the inlet 13, the process of exhausting the cleansing solution to the through hole 31 is repeatedly performed, thereby the first and second inner space 11 and 21 and through hole 31 of the cuvette 100 is effectively cleansed. The solution MS and the cleansing solution is exhausted into the through hole 31 by applying the pressure P to the inlet 13 such that the suction nozzle is not necessary.

FIGS. 9(a) to (d) show top plan views of a lower portion and a through hole applied to the cuvette of FIG. 3 according to the first to fourth exemplary embodiments. The lower portion 32 is formed with a quadrangle shape following the upper portion 12 and the middle portion 22. Through holes 311, 312, 313, and 314 according to the first to fourth exemplary embodiments may have interior diameters of various shapes.

Figure 9:
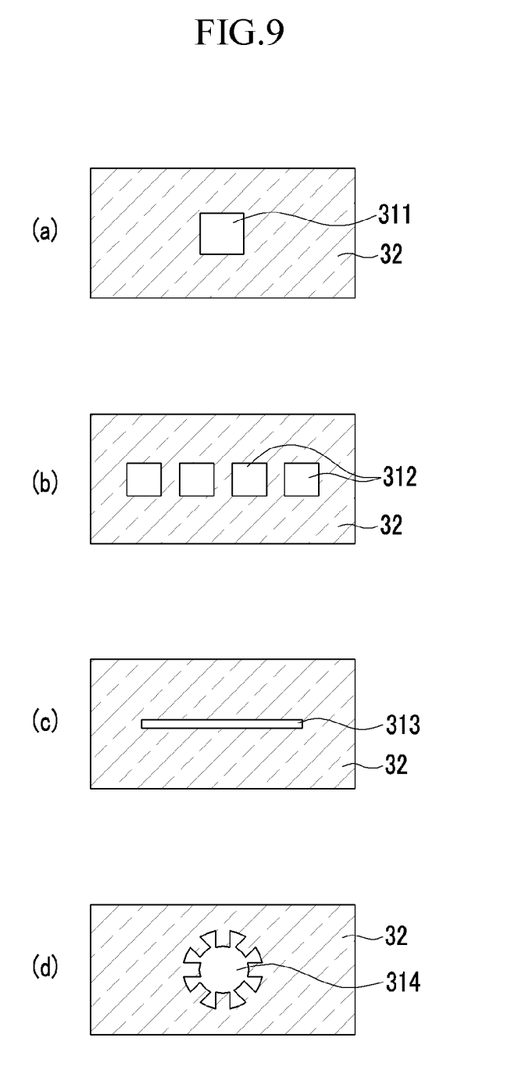
FIG. 9 is a top plan view of a lower portion and a through hole applied to the cuvette of FIG. 3 according to the first to fourth exemplary embodiments.

The through hole 311 of the first exemplary embodiment is formed with the quadrangle shape in the planar cross-section of the lower portion 32, it may be formed with a circular shape (not shown), and may be formed singularly (a).

The through hole 312 of the second exemplary embodiment is formed with a plurality of through holes 311 that are like the first exemplary embodiment such that the cleansing process may be effectively performed compared with the single through hole 311 of the first exemplary embodiment. The through hole 312 of the second exemplary embodiment may be formed in plural in an area range of the bottom surface 23 of the second inner space 21.

By the weight of the solution MS, each force (pressure) applied to the through holes 311, 312, 313, and 314 is proportional to the area, and by the surface tension, the capillary force blocking the solution MS in the through holes 311, 312, 313, and 314 is proportional to the length contacting the solution MS. Accordingly, although the through holes 311, 312, 313, and 314 have interior diameters of the same area, when the length contacting the solution MS is elongated, the effect of the capillary force is increased, thereby ensuring a larger pressure. That is, the solution MS may be stopped.

For example, the through hole 313 of the third exemplary embodiment is formed with a slit shape 43 that is set up to be long in one side while having a narrow width in the planar cross-section of the lower portion 32(c), and the through hole 314 of the fourth exemplary embodiment has a curved inner surface or a minute structure to maximizing the effect of the capillary force.

In general, most products made of a plastic-containing material among the containers used for the biochemical test are mass-produced through injection molding such that the cost thereof is low. The cuvette 100 of an exemplary embodiment may be basically manufactured through injection molding.

The cuvette 100 may include a non-wetting coating layer (not shown) formed at the surface of the interior diameter of the through hole 31 according to the material of the injection molding. For example, the non-wetting coating layer may be formed with a polytetrafluoroethylene (PTFE, Teflon®) coating or a fluorocarbon-based polymer coating, for example, parylene. The capillary force is proportional to the length contacting the solution MS, and is also proportional to the angle formed in the surface contacted with the solution MS, that is, the contact angle. Accordingly, if the contact angle is increased by the non-wetting coating layer, the effect of the capillary force may be increased.

Figure 10:
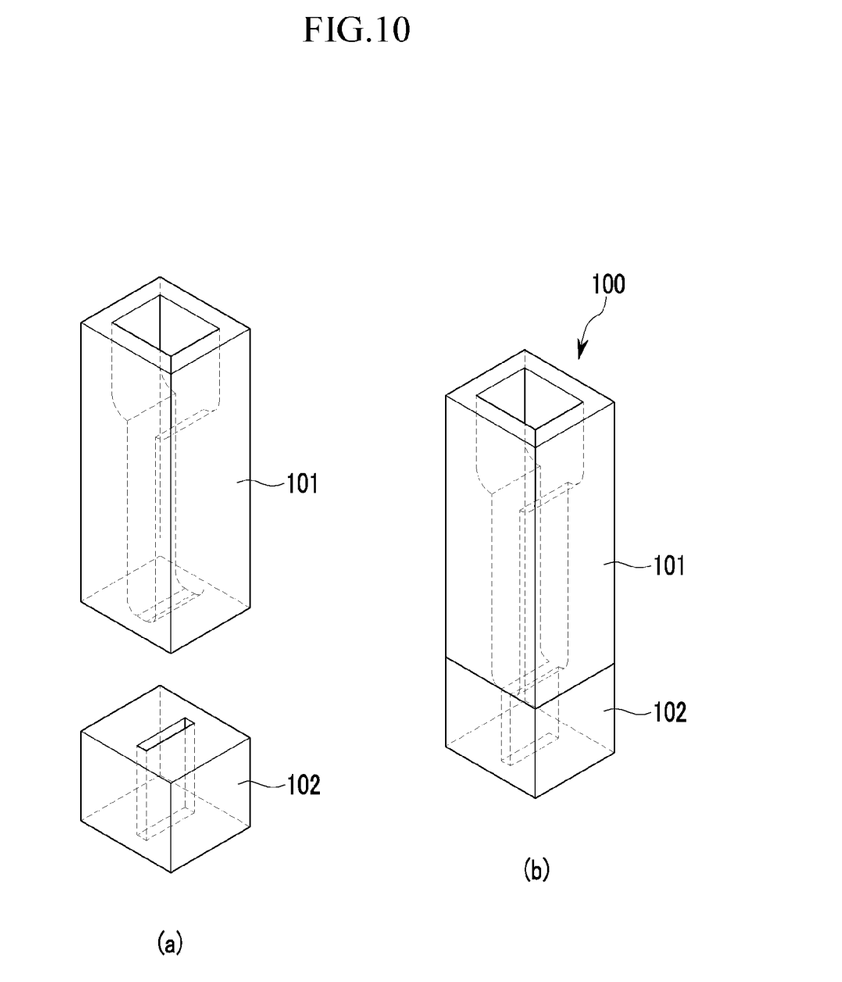
FIG. 10 is a perspective view of a body unit and a through hole unit before and after a combination among a manufacturing process of the cuvette of FIG. 3.

FIGS. 10(a) and (b) show perspective views of a body unit and a through hole unit before and after combination among a manufacturing process of the cuvette of FIG. 3.

Referring to FIGS. 10(a) and (b), the cuvette 100 may be completed by separately manufacturing and combining the body unit 101 and the through hole unit 102. The through hole unit 102 may be formed with a material having an excellent non-wetting ability. The cuvette 100 may be manufactured by combining a through hole unit 102 and a body unit 101 to each other.

Figure 11:
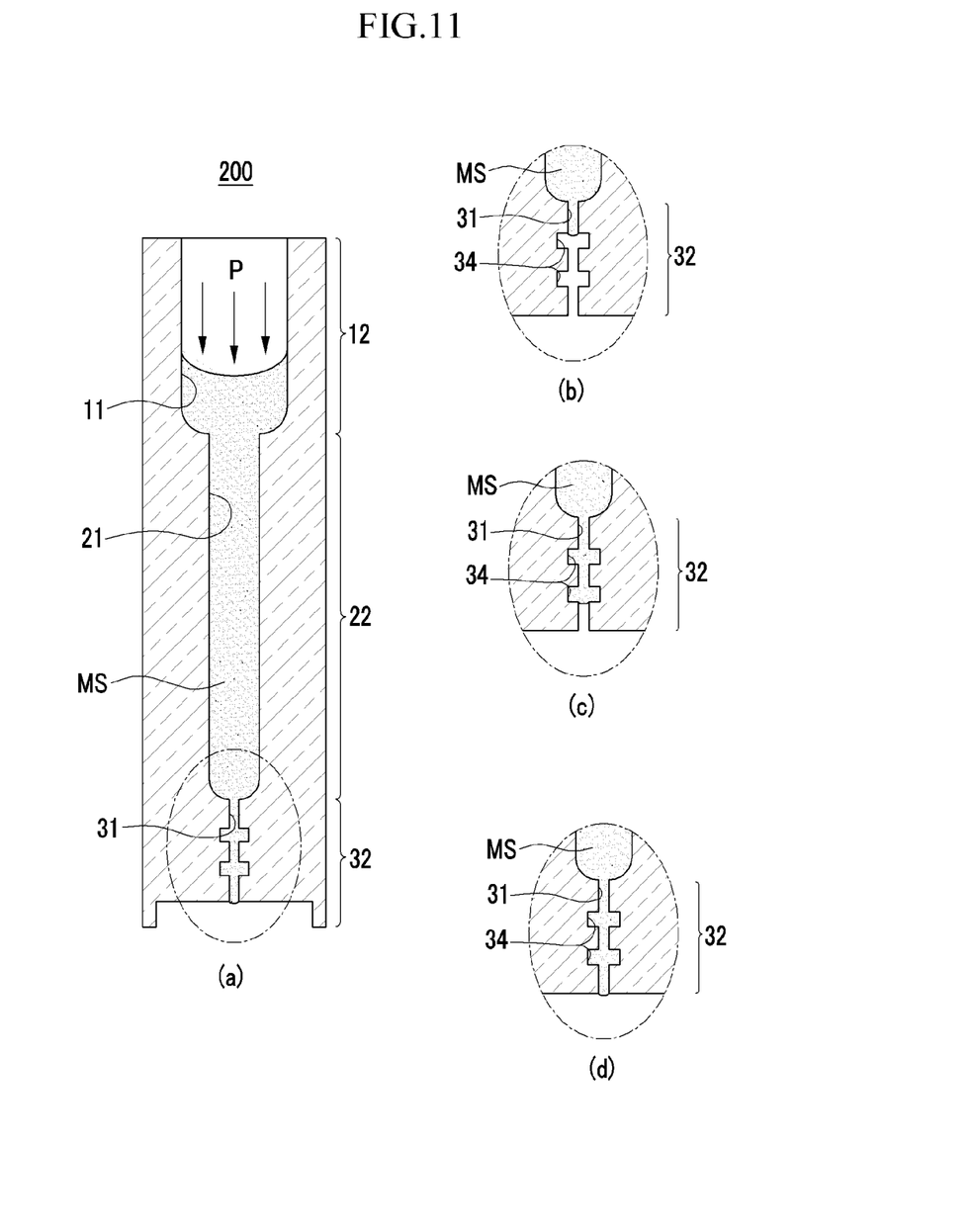
FIG. 11 is a cross-sectional view showing an operation principle of a cuvette according to another exemplary embodiment of the present invention.

FIG. 11 is a cross-sectional view showing an operation principle of a cuvette according to another exemplary embodiment of the present invention.

Referring to FIG. 11, the cuvette 200 of another exemplary embodiment may further include a groove 34 connected to the through hole 31. The through hole 31 is formed in a height direction of the cuvette 200 in the lower portion 32, and the groove 34 is formed and connected in the direction vertical to the through hole 31. The groove 34 may be formed singularly or in plural with respect to the entire length of the through hole 31.

In addition to the function of the through hole 34 stopping the solution MS and exhausting the solution MS under the cleansing, when an unexpected external impact is applied to the cuvette 200 and the lower portion 32 such that the solution MS is spread and flowed down into the through hole 34, as shown in FIGS. 8(b), (c), and (d), the groove 34 gradually receives the solution MS such that the solution MS is prevented from completely flowing down outside the through hole 34 of the cuvette 200 during the test. Accordingly, the cuvette 200 of the present exemplary embodiment may further facilitate safety of the test equipment. The shape of the groove 34 may be various and is set to not have an effect on the exhaust of the solution MS under the cleansing as well as the function of the safety apparatus. That is, the groove 34 is set up for the solution MS to not to remain after the exhausting.

Figure 12:
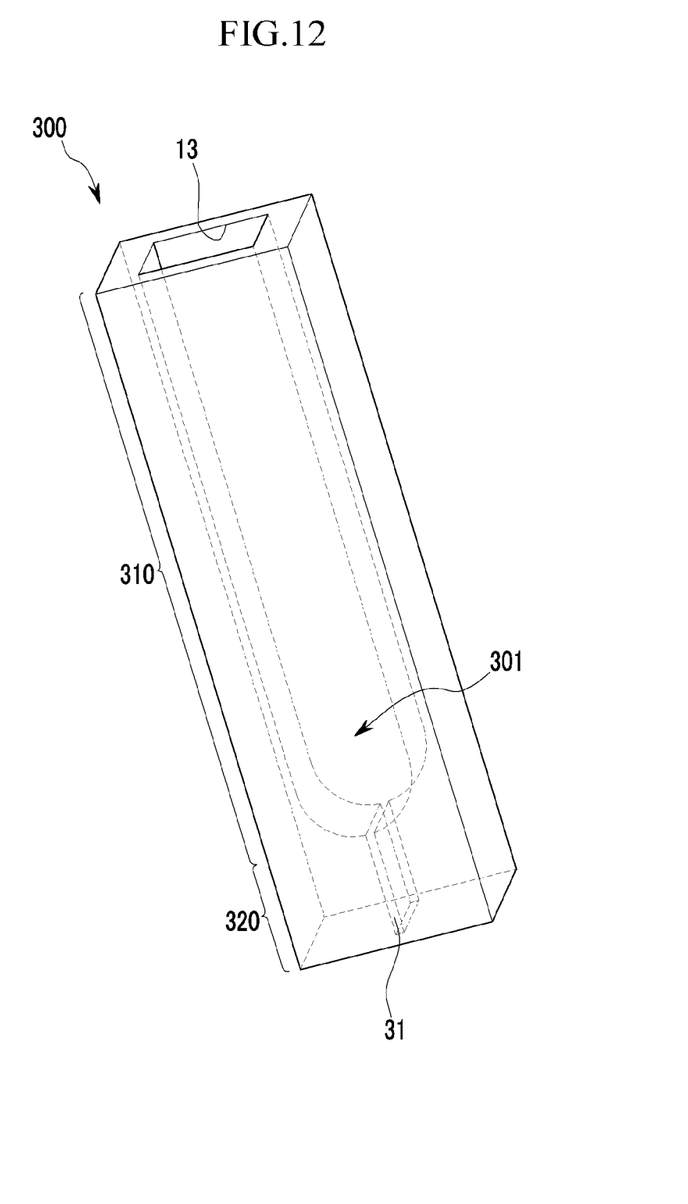
FIG. 12 is a perspective view of a cuvette according to another exemplary embodiment of the present invention.

FIG. 12 is a perspective view of a cuvette according to another exemplary embodiment of the present invention.

Referring to FIG. 12, in a cuvette 300 according to the present exemplary embodiment, an inner space 301 is formed in an upper portion 310 and a through hole 31 connected to a path having a narrower area than a horizontal cross-section of the inner space 301 is formed in a lower portion 320 while being connected to the inner space 301. That is, the horizontal cross-section of the inner space 301 is formed equally to the area of an inlet 13 throughout the entire length, but a portion connected to the through hole 31 is formed to be rounded at both corner portions.

The cuvette 300 according to the present exemplary embodiment may include the through hole having the various cross-sections as shown in FIG. 9, and may also further include a groove connected to the through hole as shown in FIG. 11.

Figure 13:
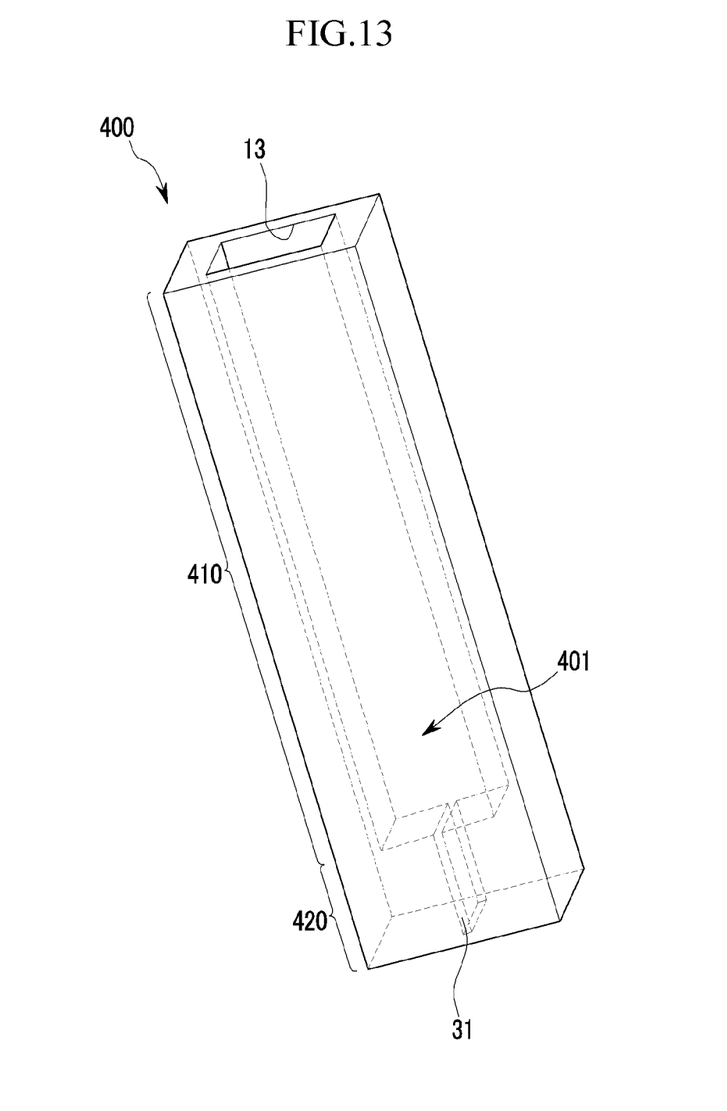
FIG. 13 is a perspective view of a cuvette according to another exemplary embodiment of the present invention.

FIG. 13 is a perspective view of a cuvette according to another exemplary embodiment of the present invention.

Referring to FIG. 13, in a cuvette 300 according to the present exemplary embodiment, an inner space 401 is formed in an upper portion 410 and a through hole 31 connected to a path having a narrower area than a horizontal cross-section of the inner space 401 is formed in a lower portion 420 while being connected to the inner space 401. That is, the horizontal cross-section of the inner space 401 is formed equally to the area of an inlet 13 throughout the entire length.

The cuvette 400 according to the present exemplary embodiment may also include the through hole having the various cross-sections as shown in FIG. 9, and may also further include a groove connected to the through hole as shown in FIG. 11.

While this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims.

The invention claimed is:

1. A cuvette made of a container used for a spectroscope test of a sample solution, comprising:
an upper portion having an inlet and forming a first inner space of the container;
a middle portion connected to the first inner space and forming a second inner space of the container configured to contain the sample solution; and
a lower portion having a through hole connected to the second inner space, a horizontal cross-section area of the through hole being narrower than a horizontal cross-section area of the second inner space,
wherein the vertical length of the second inner space is longer than the vertical length of the through hole,
wherein the lower portion and the middle portion have a quadrangle outer shape and the lower portion has substantially the same outer width and outer thickness with the middle portion, and
wherein the horizontal cross-section areas of the second inner space and the through hole respectively have a first dimension and a second dimension, the first dimension of the second inner space is the same to the first dimension of the through hole and the second dimension of the second inner space is greater than the second dimension of the through hole.

2. The cuvette of claim 1, wherein
the through hole has a function as a valve that is closed by a capillary force and is opened by an added pressure.

3. The cuvette of claim 1, wherein
the through hole is formed for a surface tension acting between the sample solution and an inner surface of the through hole to be equal or larger than gravity applied to the sample solution included in the container.

4. The cuvette of claim 1, wherein
the through hole and the inlet are satisfied with a condition below:

$$\rho g H \leq -2\sigma\left(\frac{\cos\theta_i}{w_2} + \frac{\cos\theta_i}{h_2} - \frac{\cos\theta_r}{w_1} - \frac{\cos\theta_r}{h_1}\right),$$

wherein $w_1$ is a width of an inlet of an upper portion, $h_1$ is a thickness of an inlet of an upper portion, $w_2$ is a width of a through hole, $h_2$ is a thickness of a through hole, $\rho$ is a density of a liquid, g is gravity acceleration, and H is a difference of a height in a gravity direction formed by a liquid.

5. The cuvette of claim 1, wherein:
the horizontal cross-section area of the second inner space is smaller than the horizontal cross-section area of the first inner space.

6. The cuvette of claim 1, wherein
the width of the second inner space is larger than the width of a sensor.

7. The cuvette of claim 5, wherein
the cuvette is formed by combining a body unit of which the upper portion and the middle portion are integrally formed, and a through hole unit forming the lower portion.

8. The cuvette of claim 7, wherein
the through hole unit is formed of a non-wetting material.

9. The cuvette of claim 1, wherein,
for the through hole, the horizontal cross-section of the lower portion is formed with a quadrangular shape or a circular shape.

10. The cuvette of claim 1,
wherein a plurality of through holes formed in the lower portion are respectively connected to the second inner space, and
wherein the sum of horizontal cross-section areas of the through holes are narrower than a horizontal cross-section area of the second inner space.

11. The cuvette of claim 1, wherein
for the through hole, the horizontal cross-section of the lower portion is formed with a slit shape.

12. The cuvette of claim 1, wherein
the through hole has an inner surface that is curved or is formed with a minute structure.

13. The cuvette of claim 1, wherein
the through hole further includes a non-wetting coating layer formed at the inner surface thereof.

14. A cuvette made of a container including a sample solution and used for a spectroscope test, comprising:
an upper portion having an inlet and forming a first inner space of the container; and
a lower portion formed to communicate with the first inner space and forming a through hole having a horizontal cross-section area of the through hole is narrower than the horizontal cross-section area of the first inner space,
wherein the lower portion further includes a groove connected to the through hole.

15. The cuvette of claim 14, wherein
the groove is formed and connected in a direction vertical to the through hole.

16. The cuvette of claim 14, wherein
the groove is formed singularly or in plural with respect to an entire length of the through hole.

17. The cuvette of claim 1, wherein the inlet is configured to receive a cleansing solution such that the received cleansing solution is exhausted to the through hole for cleaning the first inner space and the second inner space when the spectroscope test of the sample solution is completed.

* * * * *